United States Patent
Zheng et al.

(10) Patent No.: US 10,970,829 B2
(45) Date of Patent: Apr. 6, 2021

(54) SYNTHESIZING AND SEGMENTING CROSS-DOMAIN MEDICAL IMAGES

(71) Applicant: Siemens Healthcare GmbH, Erlangen (DE)

(72) Inventors: Yefeng Zheng, Princeton Junction, NJ (US); Zizhao Zhang, Gainesville, FL (US)

(73) Assignee: Siemens Healthcare GmbH, Erlangen (DE)

(*) Notice: Subject to any disclaimer, the term of this patent is extended or adjusted under 35 U.S.C. 154(b) by 77 days.

(21) Appl. No.: 16/106,086

(22) Filed: Aug. 21, 2018

(65) Prior Publication Data
US 2019/0066281 A1 Feb. 28, 2019

Related U.S. Application Data

(60) Provisional application No. 62/549,442, filed on Aug. 24, 2017.

(51) Int. Cl.
*G06T 5/50* (2006.01)
*G06T 5/00* (2006.01)
(Continued)

(52) U.S. Cl.
CPC .............. *G06T 5/50* (2013.01); *G06K 9/6256* (2013.01); *G06N 3/0454* (2013.01); *G06N 3/0472* (2013.01); *G06N 3/08* (2013.01); *G06T 5/006* (2013.01); *G06T 7/11* (2017.01); *G06T 7/174* (2017.01); *G16H 30/40* (2018.01); *G16H 50/50* (2018.01); *G16H 50/70* (2018.01); *A61B 6/032* (2013.01); *A61B 6/5247* (2013.01); *A61B 6/563* (2013.01); *A61B 8/5261* (2013.01); *G06K 2209/05* (2013.01); *G06T 2207/10081* (2013.01); *G06T 2207/10088* (2013.01); *G06T 2207/10104* (2013.01);
(Continued)

(58) Field of Classification Search
CPC ....... A61B 6/5247; A61B 8/5261; G06T 5/50; G06T 5/006
See application file for complete search history.

(56) References Cited

U.S. PATENT DOCUMENTS

2016/0210749 A1* 7/2016 Nguyen .................. A61B 5/00
2017/0200067 A1* 7/2017 Zhou ..................... G06T 7/143
2018/0307947 A1* 10/2018 Choi ..................... G06T 11/60

OTHER PUBLICATIONS

Bousmalis et al., "Unsupervised Pixel-Level Domain Adaptation with Generative Adversarial Networks", IEEE, 2016, pp. 3733-3731.
(Continued)

*Primary Examiner* — John J Lee

(57) ABSTRACT

Systems and methods for generating synthesized images are provided. An input medical image of a patient in a first domain is received. A synthesized image in a second domain is generated from the input medical image of the patient in the first domain using a first generator. The first generator is trained based on a comparison between segmentation results of a training image in the first domain from a first segmentor and segmentation results of a synthesized training image in the second domain from a second segmentor. The synthesized training image in the second domain is generated by the first generator from the training image in the first domain. The synthesized image in the second domain is output.

20 Claims, 13 Drawing Sheets

(51) Int. Cl.
| | |
|---|---|
| *G06K 9/62* | (2006.01) |
| *G06T 7/174* | (2017.01) |
| *G16H 50/70* | (2018.01) |
| *G06T 7/11* | (2017.01) |
| *G16H 30/40* | (2018.01) |
| *G06N 3/04* | (2006.01) |
| *G06N 3/08* | (2006.01) |
| *G16H 50/50* | (2018.01) |
| *A61B 6/03* | (2006.01) |
| *A61B 6/00* | (2006.01) |
| *A61B 8/08* | (2006.01) |

(52) U.S. Cl.
CPC ........... *G06T 2207/10108* (2013.01); *G06T 2207/10116* (2013.01); *G06T 2207/10132* (2013.01); *G06T 2207/20081* (2013.01); *G06T 2207/20212* (2013.01); *G06T 2207/30004* (2013.01)

(56) References Cited

OTHER PUBLICATIONS

Costa et al., "Towards Adversarial Retinal Image Synthesis", Jan. 31, 2017, pp. 1-11.
Huang et al, "Simultaneous Super-Resolution and Cross-Modality Synthesis of 3D Medical Images using Weakly-Supervised Joint Convolutional Sparse Coding", 2017, pp. 6070-6079.
Ioffe et al, "Batch Normalization: Accelerating Deep Network Training by Reducing Internal Covariate Shift", International Conference on Machine Learning, 2015, pp. 1-11.
Isola et al., "Image-to-Image Translation with Conditional Adversarial Networks", 2016, pp. 1125-1134.
Johnson et al., "Perceptual Losses for Real-Time Style Transfer and Super-Resolution", European Conference on Computer Vision, 2016, pp. 1-18.
Kamnitsas et al. "Unsupervised Domain Adaption in Brain Lesion Segmentation with Adversarial Networks", International Conference on Information Processing in Medical Imaging, 2017 pp. 1-13.
Kim et al., "Learning to Discover Cross-Domain Relations with Generative Adversarial Networks", 2017, 10 pgs.
Kingma et al, "Adam: A Method for Stochastic Optimization", ICLR, 2015, pp. 1-15.
Kohl et al., "Adversarial Networks for the Detection of Aggressive Prostate Cancer", MICCAI, 2017, 8 pgs.
Liu et al., "Unsupervised Image-to-Image Translation Networks", 31st Conference on Neural Information Processing Systems, 2017, pp. 1-11.
Luc et al., "Semantic Segmentation Using Adversarial Networks", Workshop on Adversarial Training, NIPS 2016, Spain, pp. 1-12.
Nie et al., "Medical Image Synthesis with Context-Aware Generative Adversarial Networks", 2016; 12 pgs.
Odena et al., "Deconvolution and Checkerboard Artifacts", Distill 1, No. 10; Oct. 17, 2016.
Ronneberger et al., "U-Net: Convolutional Networks for Biomedical Image Segmentation", International Conference on Medical Image Computing and Computer-Assisted Intervention, May 2018, pp. 1-8.
Roth et al., "A New 2.5D Representation for Lymph Node Detection using Random Sets of Deep Convolutional Neural Network Observations", International Conference on Medical Image Computing and Computer-Assisted Intervention, Jun. 11, 2014, pp. 1-11.
Salimans et al., "Improved Techniques for Training GANs", 30th Conference on Neural Information Processing Systems, 2016, Spain, pp. 1-9.
Shrivastava, et al; "Learning from Simulated and Unsupervised Images through Adversarial Training"; 2017; CVPR. vol. 2. No. 4.; pp. 2107-2116.
Ulyanvov et al., "Instance Normalization: The Missing Ingredient for Fast Stylization", Nov. 6, 2016.
Yi et al., "DualGAN: Unsupervised Dual Learning for Image-to-Image Translation", 2017, pp. 2849-2857.
Zhang et al., "Colorful Image Colorization", European Conference on Computer Vision, Mar. 2016, pp. 1-25.
Zhu et al., "Unpaired Image-to-Image Translation using Cycle-Consistent Adversarial Networks", 2017 pp. V2223-V2232.
Bansal et al., "Understanding and Implementing CycleGAN in TensorFlow", https://hardikbansal.github.io/CycleGANBlog retrieved on Aug. 2, 2018.
Tripathy et al., "Learning Image-to-Image Translation Using Paired and Unpaired Training Samples", May 8, 2018; pp. 1-19.

\* cited by examiner

| Method | Dice score (%) | |
|---|---|---|
| | CT | MRI |
| Baseline (R) | 67.8 | 70.3 |
| ADA (R+S) | 66.0 | 71.0 |
| Online (R+S) | 74.4 | 73.2 |

| Method | S-score (%) | |
|---|---|---|
| | CT | MRI |
| G w/o SC | 66.8 | 67.5 |
| G w/ SC | 69.2 | 69.6 |

SYNTHESIZING AND SEGMENTING CROSS-DOMAIN MEDICAL IMAGES

CROSS-REFERENCE TO RELATED APPLICATIONS

This application claims the benefit of U.S. Provisional Application No. 62/549,442, filed Aug. 24, 2017, the disclosure of which is herein incorporated by reference in its entirety.

BACKGROUND

The present invention relates generally to synthesizing and segmenting medical images, and more particularly to cross-domain synthesizing and segmenting medical images using generative adversarial networks trained with adversarial learning, cycle-consistency loss, and shape-consistency loss.

In the current clinical practice, a multitude of imaging modalities may be available for disease diagnosis and surgical planning. Each of these imaging modalities captures different characteristics of the underlying anatomy and the relationship between any two modalities is highly nonlinear. These different imaging techniques provide physicians with varied tools and information for making accurate diagnoses.

Machine learning based methods have been widely used for medical imaging analysis for, e.g., the detection, segmentation, and tracking of anatomical structures. Such machine learning based methods are typically generic and can be extended to different imaging modalities by re-training the machine learning model on the target imaging modality. However, in practice, it is often difficult to collect a sufficient amount of training images, particularly for a new imaging modality not well established in clinical practice.

Cross-modal translation generates synthetic medical images in a desired target modality from images of a given source modality. Such synthetic medical images are often used as supplementary training data for training a machine learning model for medical image analysis. Conventional approaches to cross-modal translation require paired multi-modality training images from the same patient with pixel-to-pixel correspondence.

BRIEF SUMMARY OF THE INVENTION

In accordance with one or more embodiments, systems and methods for generating synthesized images are provided. An input medical image of a patient in a first domain is received. A synthesized image in a second domain is generated from the input medical image of the patient in the first domain using a first generator. The first generator is trained based on a comparison between segmentation results of a training image in the first domain from a first segmentor and segmentation results of a synthesized training image in the second domain from a second segmentor. The synthesized training image in the second domain is generated by the first generator from the training image in the first domain. The synthesized image in the second domain is output.

In accordance with one or more embodiments, the first generator for generating synthesized images in the second domain from images in the first domain, a second generator for generating synthesized images in the first domain from images in the second domain, the first segmentor for segmenting images in the first domain, and the second segmentor for segmenting images in the second domain are simultaneously trained in a training stage prior to receiving the input medical image of the patient.

In accordance with one or more embodiments, the first generator, the second generator, the first segmentor, and the second segmentor are trained by optimizing a single objective function.

In accordance with one or more embodiments, the first segmentor is trained based on synthesized training images in the first domain generated by the second generator and the second segmentor is trained based on synthesized training images in the second domain generated by the first generator.

In accordance with one or more embodiments, the input medical image of the patient in the first domain is segmented using the first segmentor. The results of the segmenting the input medical image of the patient in the first domain are output.

In accordance with one or more embodiments, a second input medical image in the second domain is received. A synthesized image in the first domain is generated from the second input medical image of the patient in second first domain using the second generator. The second generator is trained based on a comparison between segmentation results of a second training image in the second domain from the second segmentor and segmentation results of a second synthesized training image in the first domain from the first segmentor. The second synthesized training image in the first domain is generated by the second generator from the second training image in the second domain. The second synthesized image in the first domain is output.

In accordance with one or more embodiments, the second input medical image of the patient in the second domain is segmented using the second segmentor. Results of the segmenting the second input medical image of the patient in the second domain are output.

In accordance with one or more embodiments, first generator is trained based on unpaired training images in the first domain and the second domain.

In accordance with one or more embodiments, outputting the synthesized image in the second domain comprises displaying the synthesized image on a display device.

These and other advantages of the invention will be apparent to those of ordinary skill in the art by reference to the following detailed description and the accompanying drawings.

BRIEF DESCRIPTION OF THE DRAWINGS

FIG. 7 shows a table evaluating segmentors trained using a baseline approach, an offline ADA approach, and the online approach described in accordance with embodiments of the invention;

FIG. 12 shows a table comparing generators trained without shape consistency (G w/o SC) and generators trained with shape consistence (G w/SC) according to embodiments of the invention.

DETAILED DESCRIPTION

The present invention generally relates to methods and systems for automated, computer-based synthesizing and segmenting cross-domain medical images. Embodiments of the present invention are described herein to give a visual understanding of methods for synthesizing and segmenting multimodal medical images. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Further, it should be understood that while the embodiments discussed herein may be discussed with respect to synthesizing and segmenting cross-domain medical images, the present invention is not so limited. Embodiments of the present invention may be applied for synthesizing and segmenting any type of image.

Figure 1:
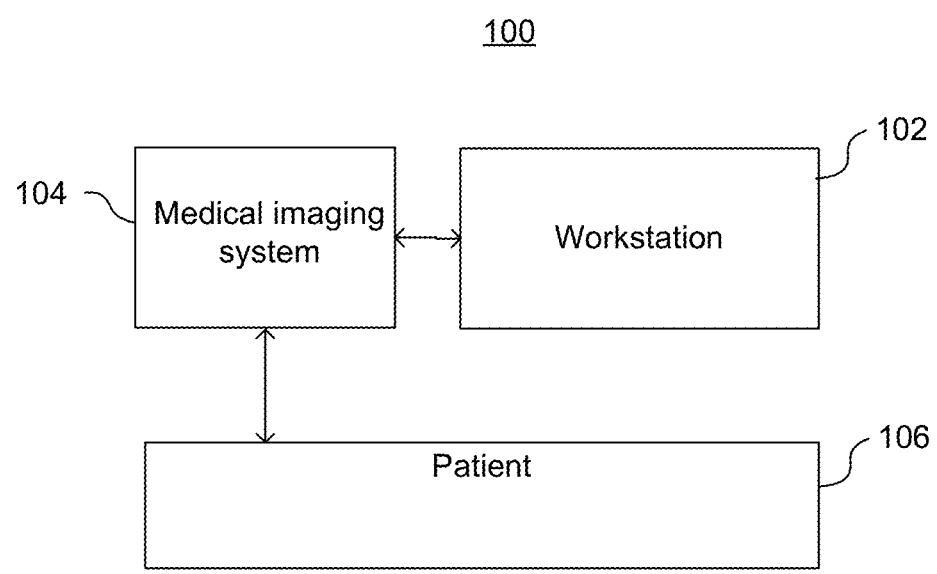
FIG. 1 shows an illustrative system for analyzing medical images, in accordance with one or more embodiments.

FIG. 1 shows a system 100 configured for analyzing medical images, in accordance with one or more embodiments. System 100 includes workstation 102, which may be used for assisting a clinician (e.g., a doctor, a medical professional, or any other user) for performing a medical evaluation on a subject or patient 106. Workstation 102 may be implemented using any suitable computing device, such as, e.g., computer 1302 of FIG. 13.

Workstation 102 may assist the clinician in performing a medical evaluation of patient 106 by performing one or more clinical tests. For example, workstation 102 may receive images of patient 106 from one or more medical imaging systems 104 for performing the clinical test. Medical imaging system 104 may be of any domain, such as, e.g., x-ray, magnetic resonance imaging (MRI), computed tomography (CT), ultrasound (US), single-photon emission computed tomography (SPECT), positron emission tomography (PET), or any other suitable domain or combination of domains. In another embodiment, workstation 102 may receive the images by loading previously stored images of the patient acquired using medical imaging system 104.

As used herein, a particular "domain" associated with a medical image refers to the modality of the medical image, such as x-ray, MRI, CT, ultrasound, etc., as well as the protocol used for obtaining the medical image in that modality, such as, e.g., MR images with different protocols (e.g., T1 and T2), contrast CT images and non-contrast CT images, CT images captured with low kV and CT images captured with high kV, or low and high resolution medical images. That is, a "first domain" and "second domain" may be completely different medical imaging modalities or different image protocols within the same overall imaging modality.

Medical image analysis is widely performed using machine learning models to, e.g., generate synthesized medical images in one domain from a medical image in another domain and to segment medical images. In clinical practice, medical evaluation of patient 106 may be improved by using images of different domains. Such machine learning models may be re-trained for image analysis of a target domain. However, in practice, it is often difficult to collect a sufficient amount of training images in the target domain to train the machine learning model.

Embodiments of the present invention provide for cross-domain synthesizing and segmenting of medical images. In an advantageous embodiment, generators for generating synthesized medical images are trained with adversarial learning, cycle-consistency loss, and shape-consistency loss and segmentors for segmenting medical images are trained using synthesized images generated by the generators. The generators and segmentors are jointly trained in an end-to-end training approach using unpaired training images. Embodiments of the present invention thereby provide synthetic, realistic looking medical images using unpaired training data, minimize the geometric distortion in cross-domain translation, and improve the segmentation accuracy of domains with limited training samples.

Figure 2:
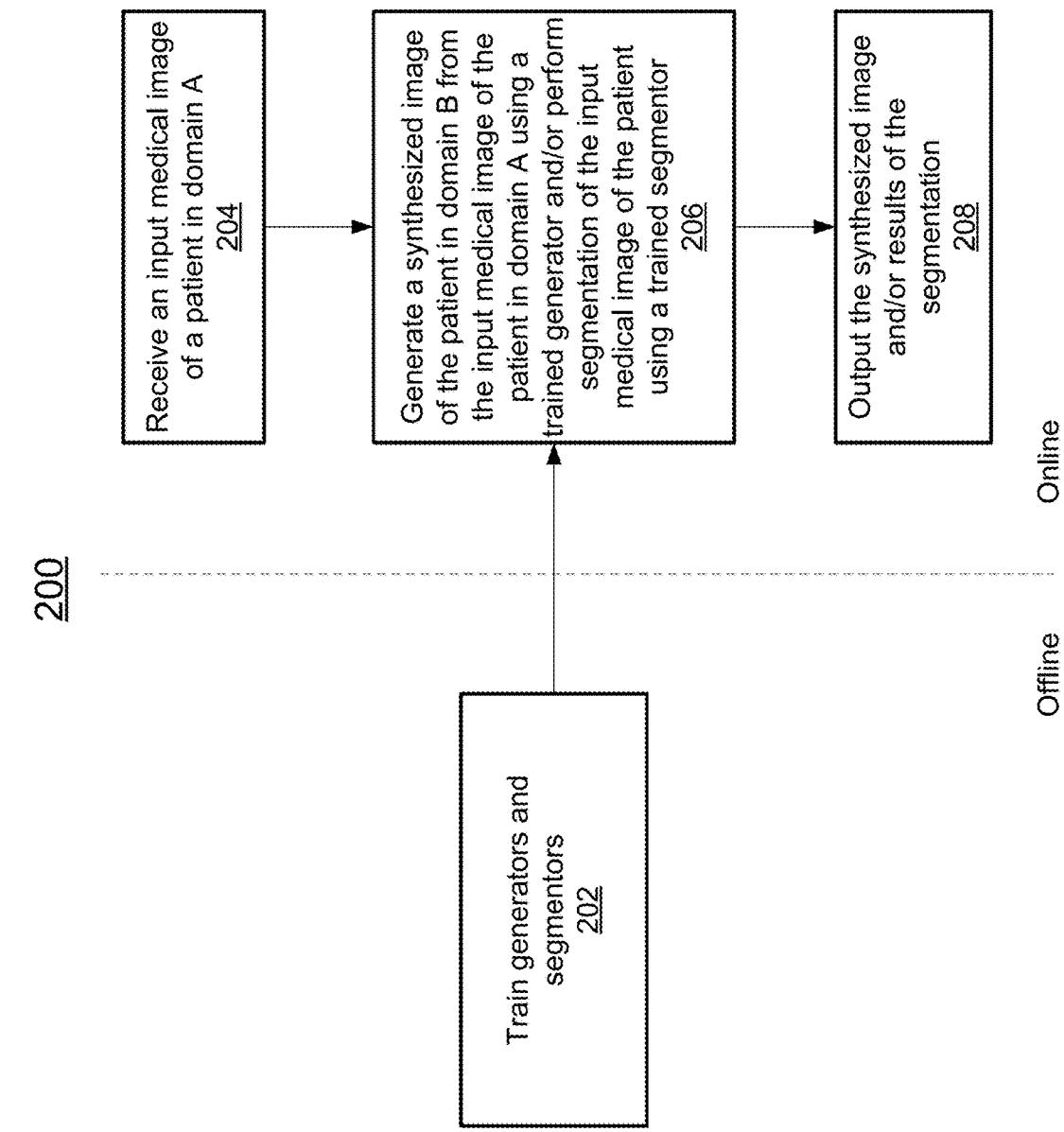
FIG. 2 shows a workflow for training and applying machine learning models for cross-domain synthesizing and segmenting of medical images, in accordance with one or more embodiments.

FIG. 2 shows a high-level workflow 200 for training and applying machine learning models for cross-domain synthesizing and segmenting of medical images, in accordance with one or more embodiments. Block 202 shows an offline or training stage for training generators and segmentors. Blocks 204-208 show an online or testing stage for applying the trained generators and segmentors. In one embodiment, workflow 200 is implemented by a computing device, such as, e.g., workstation 102 of FIG. 1.

At block 202, during an offline stage, generators for generating a synthesized medical image and segmentors for segmenting a medical image are simultaneously trained. In one embodiment, the generators that are trained at block 202 include a first generator for generating a synthesized medical image in domain B (also referred to as a first domain) from a medical image in domain A (also referred to as a second domain) and a second generator for generating a synthesized medical image in domain A from a medical image in domain B, and the segmentors that are trained at block 202 include a first segmentor for segmenting a medical image in domain A and a second segmentor for segmenting a medical image in domain B. Domains A and B may be any suitable, but different, domains, such as, e.g., CT, MR, DynaCT, ultrasound, PET, etc. The generators and segmentors are simultaneously trained in a mutually beneficial, end-to-end training stage using unpaired training data. For example, the generators and segmentors may be trained by optimizing a single objective function.

In one embodiment, the first and second generators are trained with shape consistency. For example, the first generator is trained based on a comparison between segmentation results of a training image in the first domain (domain A) from the first segmentor and segmentation results of a synthesized training image in the second domain (domain B) from the second segmentor, where the synthesized training image in the second domain (domain B) is generated by the first generator from the training image in the first domain (domain A). The second generator is trained based on a comparison between segmentation results of a training image in the second domain (domain B) from the second segmentor and segmentation results of a synthesized training image in the first domain (domain A) from a first segmentor, where the synthesized training image in the first domain (domain A) is generated by the second generator from the training image in the second domain (domain B).

In one embodiment, the first and second segmentors are trained using both real training images and synthesized training images. For example, the first segmentor is trained based on synthesized training images in the first domain generated by the second generator and the second segmentor is trained based on synthesized training images in the second domain generated by the first generator.

Training of the generators and segmentors is described in further detail below with respect to FIGS. 3 and 4.

At block 204, during an online stage, an input medical image of a patient in domain A is received. The input medical image may be received directly from an image acquisition device used to acquire the input medical image, such as, e.g., medical imaging system 104 of FIG. 1. Alternatively, the input medical image may be received by loading a previously acquired medical image from a storage or memory of a computer system or receiving a medical image that has been transmitted from a remote computer system.

At block 206, a synthesized image of the patient in domain B is generated from the input medical image of the patient in domain A using a respective trained generator (trained at step 202) and/or a segmentation of the input medical image of the patient is performed using a respective trained segmentor (trained at step 202).

At block 208, the synthesized image of the patient in domain B and/or the results of the segmentation of the input medical image of the patient are output. For example, the synthesized image and/or the results of the segmentation can be output by displaying the synthesized image and/or segmentation results on a display device of a computer system, storing the synthesized image and/or the results of the segmentation on a memory or storage of a computer system, or by transmitting the synthesized image and/or the results of the segmentation to a remote computer system.

It should be understood that once the generators and segmentors are trained in the training stage, the blocks 204-208 of the online stage can be repeated for each newly received medical image(s) to perform cross-domain synthesizing and segmenting using the trained generators and segmentors. For example, blocks 204-208 can be repeated for a second medical input image of a patient in domain B.

Figure 3:
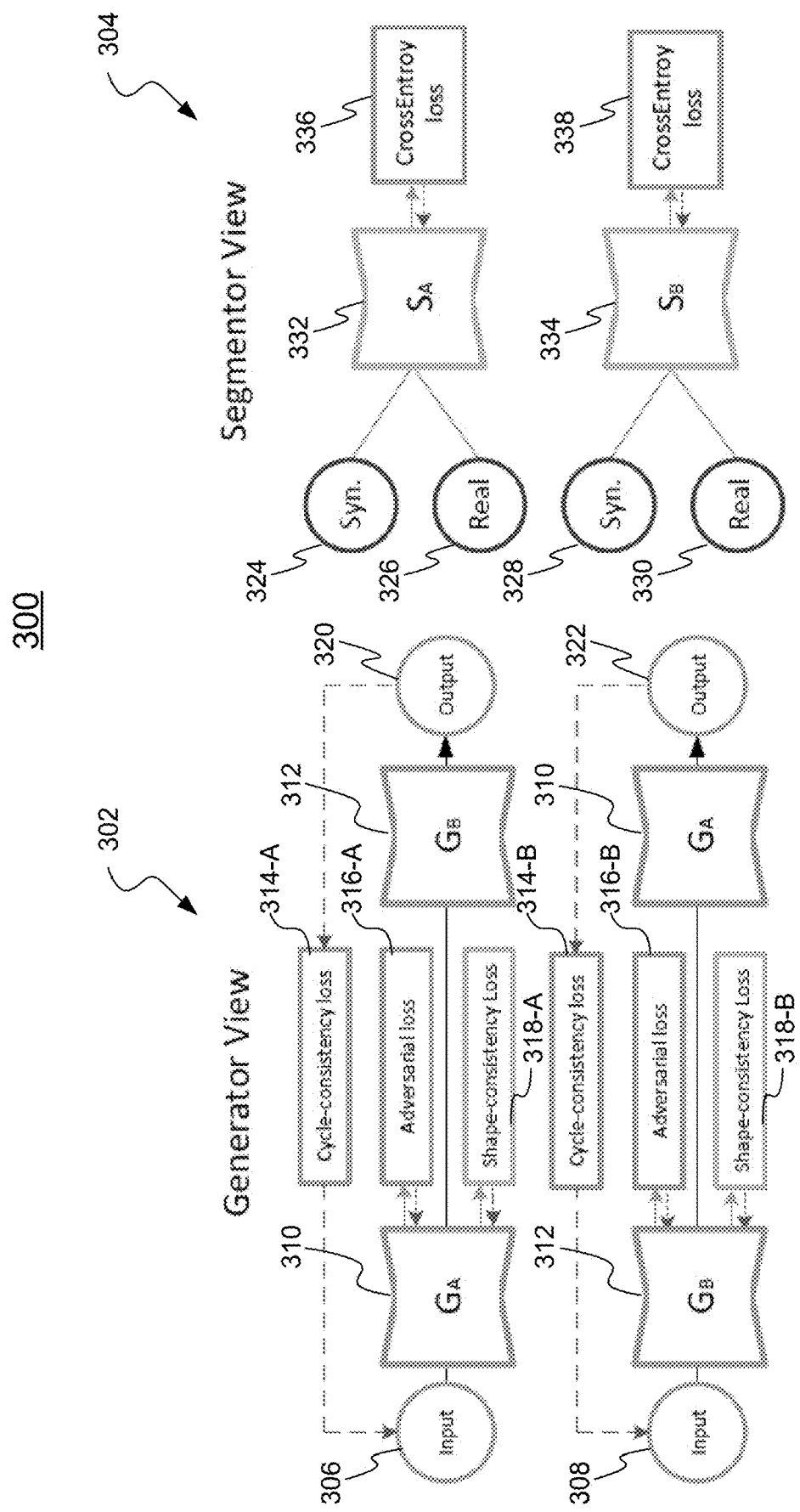
FIG. 3 shows a functional block diagram 300 for training generators and segmentors during an offline stage, in accordance with one or more embodiments.

FIG. 3 shows a high-level functional block diagram 300 for training generators and segmentors during an offline stage, in accordance with one or more embodiments. In one embodiment, functional block diagram 300 shows functional components for jointly training generators and segmentors for performing step 202 of FIG. 2. While certain components are depicted as multiple instances in functional block diagram 300 to facilitate the illustration of the functional components for training the generators and segmentors, it should be understood such components are implemented in a single, end-to-end training of the generators and segmentors.

Generator view 302 shows functional components for training generator $G_A$ 310 for generating synthesized medical images in domain A from an input medical image in domain B and generator $G_B$ 312 for generating synthesized medical images in domain B from an input medical image in domain A. Generators $G_A$ 310 and $G_B$ 312 are trained using a set of training images $I_B$ 306 in domain B and a set of training images $I_A$ 308 in domain A. Training images $I_A$ 306 and $I_B$ 308 are real images that are unpaired (i.e., training images $I_A$ 306 and $I_B$ 308 are of different patients). Generators $G_A$ 310 and $G_B$ 312 are each implemented as a generator network of a respective GAN.

Generators $G_A$ 310 and $G_B$ 312 are trained using adversarial loss functions 316-A and 316-B, respectively, denoted as discriminator networks $D_A$ and $D_B$, respectively. Discriminator $D_A$ 316-A aims to distinguish between the synthesized image in domain A generated by generator $G_A$ 310 and a real image in domain A from training images 308, and classifies one image as real and the other as fake. Discriminator $D_B$ 316-B aims to distinguish between the synthesized image in domain B generated by generator $G_B$ 312 and a real image in domain B from training images 306, and classifies one image as real and the other as fake. Adversarial loss functions 316-A and 316-B will guide generators $G_A$ 310 and $G_B$ 312 to generate synthesized images that are indistinguishable from the real training images 306 and 308 in their corresponding domain.

GANs typically require paired training data for pixel-wise reconstruction between images of different domains. To bypass the infeasibility of pixel-wise reconstruction with paired data, cycle consistency is introduced as cycle-consistency loss functions 314-A and 314-B to encourage the cascaded translations provided by generators $G_A$ 310 and $G_B$ 312 to reproduce the original image, similar to what was implemented in CycleGAN. According to cycle consistency, an image in domain A translated to domain B as a synthesized image by generator $G_B$ 312 and translated back to domain A as a synthesized image by generator $G_A$ 310 should return the initial image in domain A. Similarly, an image in domain B translated by generator $G_A$ 310, which is then translated by generator $G_B$ 312 should return the initial image in domain B. As such, cycle-consistency loss function 314-A compares the synthesized image in domain B generated by generator $G_B$ 312 (which was generated from the synthesized image in domain A generated by generator $G_A$ 310, which was generated from a real image $x_B$ from the set of training images $I_B$ 306 in domain B, i.e., $G_B(G_A(x_B))$) with that real image $x_B$ in domain B. Cycle-consistency loss function 314-B compares the synthesized image in domain A generated by generator $G_A$ 310 (which was generated from the synthesized image in domain B generated by generator $G_B$ 312, which was generated from a real image $x_A$ in domain A from the set of training images $I_A$ 308 in domain A, i.e., $G_A(G_B(x_A))$) with that real image $x_A$ in domain A.

Cycle consistency loss functions 314-A and 314-B do not account for geometric transformations by the generators when translating an image from one domain to another. In particular, when an image is translated from a source domain to a target domain, it can be geometrically distorted. However, the distortion is recovered when it is translated back to the source domain due to cycle consistency. Additionally, a certain amount of geometric transformation does not change the realness of a synthesized image and is therefore not penalized by adversarial loss functions 316-A and 316-B. To account for geometric transformation, shape-consistency loss functions 318-A and 318-B are introduced to encourage generators $G_A$ 310 and $G_B$ 312 to reproduce the original input image without geometric distortion. Shape-consistency loss function 318-A compares the segmentation of the synthesized image in domain A generated by generator $G_A$ 310 from real image $x_B$ in domain B in training images 306 with the segmentation of that real image $x_B$ in domain B. Shape-consistency loss function 318-B compares the segmentation of the synthesized image in domain B generated by generator $G_B$ 312 from real image $x_A$ in domain A in training images 308 with the segmentation of that real image $x_A$ in domain A. The segmentations are performed by a corresponding segmentor $S_A$ 332 and $S_B$ 334.

Segmentor view 304 shows functional components for training segmentors $S_A$ 332 and $S_B$ 334. To improve generalization, the segmentors are trained using both real images and synthesized images. Accordingly, segmentor $S_A$ 332 is trained using both real images 326 in domain A (e.g., training images 308) and synthesized images 324 in domain A (generated by generator $G_A$ 310). Segmentor $S_B$ 334 is trained using both real images 330 in domain B (e.g., training images 306) and synthesized images 328 in domain B (generated by generator $G_B$ 312). Segmentators $S_A$ 332 and $S_B$ 334 are trained with cross entropy loss functions 236 and 238, respectively, to encourage accurate segmentation by segmentators $S_A$ 332 and $S_B$ 334. Cross entropy loss functions 336 and 338 compare the segmentation of an image (real or synthetic) with the ground truth segmentation of that image. The ground truth segmentation of a synthetic image is the ground truth segmentation of the real image from which the synthetic image was generated from.

Figure 4:
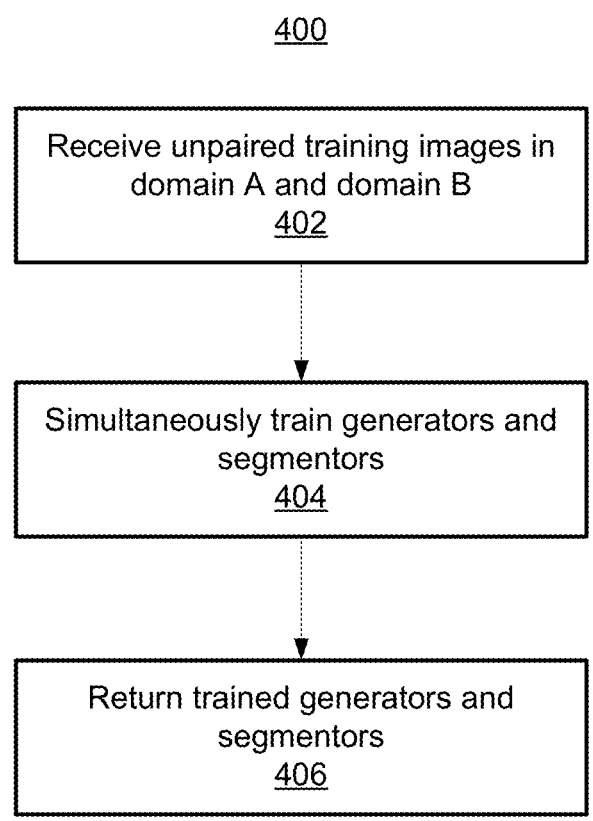
FIG. 4 shows a method for training generators and segmentors, in accordance with one or more embodiments.

FIG. 4 shows a method 400 for training generators and segmentors, in accordance with one or more embodiments. In one embodiment, method 400 implements the functional components of FIG. 3 for training generators and segmentors.

At step 402, unpaired training images in domain A and domain B are received. The training images are denoted as a set of training images $I_A$ in domain A and a set of training images $I_B$ in domain B.

At step 404, generators and segmentors are simultaneously trained. In one embodiment, a pair of generators is trained to provide an inverse mapping between domains A and B. Generator $G_A$ provides a mapping of a medical image in domain B to a synthesized image in domain A, denoted as $G_A$: B→A. Generator $G_B$ provides a mapping of an medical image in domain A to a synthesized image in domain B, denoted as $G_B$: A→B. Generators $G_A$ and $G_B$ are each defined as a generator network of a respective GAN.

Generators $G_A$ and $G_B$ are trained with adversarial loss using discriminator networks $D_A$ and $D_B$, respectively. Discriminators $D_A$ and $D_B$ encourage their corresponding generators $G_A$ and $G_B$ to generate realistic images in their respective domains. In particular, discriminator $D_A$ compares a synthesized image $Y_A$ in domain A generated by generator $G_A$ to some real image $x_A$ from the set of training images $I_A$ in domain A. Discriminator $D_B$ compares a synthesized image $Y_B$ in domain B generated by generator $G_B$ to some real image $x_B$ from the set of training images $I_B$ in domain B. The discriminators classify one image as real and the other as fake (i.e., synthesized). Generator $G_A$: B→A and its discriminator $D_A$ are expressed as the objective of Equation (1) and generator $G_B$: A→B and its discriminator $D_B$ are expressed as the objective of Equation (2).

$$\mathcal{L}_{GAN}(G_A,D_A)=\mathbb{E}_{x_A \sim P_d(x_A)}[\log D_A(x_A)]+\mathbb{E}_{x_B \sim P_d(x_B)}[\log(1-D_A(G_A(x_B)))] \quad (1)$$

$$\mathcal{L}_{GAN}(G_B,D_B)=\mathbb{E}_{x_B \sim P_d(x_B)}[\log D_B(x_B)]+\mathbb{E}_{x_A \sim P_d(x_A)}[\log(1-D_B(G_B(x_A)))] \quad (2)$$

where $x_A$ is a sample image in domain from the set of training images $I_A$ and $x_B$ is a sample image in domain B from the set of training images $I_B$.

GANs typically require paired training data for pixel-wise reconstruction between images of different domains. To bypass the infeasibility of pixel-wise reconstruction with paired data, $G_B(x_A) \approx x_B$ or $G_A(x_B) \approx x_A$, cycle-consistency loss is introduced such that $G_A(G_B(x_A)) \approx x_A$ and $G_B(G_A(x_B)) \approx x_B$. The idea is that the synthesized images in the target domain could return back to the exact images in the source domain it is generated from. Cycle-consistency loss compares real training image $x_B$ with synthesized image $Y_B$ (generated by translating $x_B$ to synthesized image $Y_A$ via generator $G_A$, and translating synthesized image $Y_A$ to synthesized image $Y_B$ via generator $G_B$, i.e., $Y_B=G_B(G_A(x_B))$). Similarly, cycle-consistency loss compares real training image $x_A$ with synthesized image $Y_A$ (generated by translating $x_A$ to synthesized image $Y_B$ via generator $G_B$, and translating synthesized image $Y_B$ to synthesized image $Y_A$ via generator $G_A$, i.e., $Y_A=G_A(G_B(x_A))$). Cycle-consistency loss for generators $G_A$ and $G_B$ is defined by the following loss function in Equation (3).

$$\mathcal{L}_{GAN}(G_A,G_B)=\mathbb{E}_{x_A \sim P_d(x_A)}[\|G_A(G_B(x_A))-x_A\|_1]+\mathbb{E}_{x_B \sim P_d(x_B)}[\|G_B(G_A(x_B))-x_B\|_1] \quad (3)$$

where $x_A$ is a sample image in domain from the set of training images $I_A$ and $x_B$ is a sample image in domain B from the set of training images $I_B$. The loss function uses the L1 loss on all voxels, which shows better visual results than the L2 loss.

Cycle-consistency has an intrinsic ambiguity with respect to geometric transformations. For example, suppose generators $G_A$ and $G_B$ are cycle consistent (i.e., $G_A(G_B(x_A))=x_A$ and $G_B(G_A(x_B))=X_B$). Let T be a bijective geometric transformation (e.g., translation, rotation, scaling, or nonrigid transformation) with inverse transformation $T^{-1}$. $G'_A=G_A \circ T$ and $G'_B=G_B \circ T^{-1}$ also cycle consistent, where $\circ$ denotes the concatenation operation of two transformations. Accordingly, when an image is translated from a source domain to target domain, cycle-consistency loss provides that the image can be geometrically distorted and the distortion can be recovered when it is translated back to the source domain without provoking any penalty in data fidelity cost. As such, cycle-consistent loss does not account for geometric transformations by the generators when translating an image from one domain to another. Additionally, a certain amount of geometric transformation does not change the realness of a synthesized images and therefore is not penalized by discriminator networks $D_A$ and $D_B$.

To address the geometric transformations that occur during translation, shape consistency loss is introduced. Shape consistency loss is applied as extra supervision on generators $G_A$ and $G_B$ to correct the geometric shapes of the synthesized images they generate. Shape consistency loss is enforced by segmentors $S_A$ and $S_B$, which map the synthesized images into a shared shape space (i.e., a label space) and compute pixel-wise semantic ownership. Segmentors $S_A$ and $S_B$ are each represented by a respective convolutional neural network (CNN). Shape consistency loss compares the segmented shape of real image $x_A$ using segmentor $S_A$ (i.e., $S_A(x_A)$) with the segmented shape of the synthetic image $Y_B$ generated by generator $G_B$ from that real image $x_A$ using from segmentor $S_B$ (i.e., $S_B(G_B(x_A))$). Similarly, shape consistency loss compares the segmented shape of real image $x_B$ using segmentor $S_B$ (i.e., $S_B(x_B)$) with the segmented shape of the synthetic image $Y_A$ generated by generator $G_A$ from that real image $x_B$ using from segmentor $S_A$ (i.e., $S_A(G_A(x_B))$). Shape-consistency loss for generators $G_A$ and $G_B$ and segmentors $S_A$ and $S_B$ is defined by the following loss function in Equation (4).

$$\mathcal{L}_{shape}(S_A, S_B, G_A, G_B) = \mathbb{E}_{x_B \sim P_d(x_B)}\left[-\frac{1}{N}\sum_i y_A^i \log(S_A(G_A(x_B))_i)\right] + \mathbb{E}_{x_A \sim P_d(x_A)}\left[-\frac{1}{N}\sum_i y_B^i \log(S_B(G_B(x_A))_i)\right] \quad (4)$$

where segmentors $S_A$: A→Y and $S_B$: B→Y produce shape space data Y (i.e., a segmentation mask) for domain A and domain B images, respectively. A standard negative log-likelihood loss is used. $y_A$, $y_B \in Y$ denotes the shape representation where $y_A^i$ and $y_B^i \in \{0, 1, \ldots, C\}$ represents one voxel with one out of C different classes. N is the total number of voxels.

To improve generalization, the synthesized data generated by generators $G_A$ and $G_B$ are used to provide extra training data for training segmentators $S_A$ and $S_B$. Segmentators $S_A$ and $S_B$ are trained using both real images and synthesized images in an online manner by joint training segmentators $S_A$ and $S_B$ with generators $G_A$ and $G_B$. Accordingly, segmentor $S_A$ is trained using both real training images $I_A$ in domain A and synthesized images $Y_A$ in domain A generated by generator $G_A$ and segmentor $S_B$ is trained using both real training images $I_B$ in domain B and synthesized images $Y_B$ in domain B generated by generator $G_B$. Segmentators $S_A$ and $S_B$ are trained with cross entropy loss to encourage accurate segmentation results. Cross entropy loss compares the segmentation results (e.g., a segmentation mask) generated by segmentators $S_A$ and $S_B$ from an image (real or synthesized) with their ground truth segmentation. The ground truth segmentation of a synthetic image is the ground truth segmentation of the real image from which the synthetic image was generated from.

A composite objective function is defined below in Equation (5) to jointly train generators $G_A$ and $G_B$ and segmentators $S_A$ and $S_B$ in an end-to-end manner.

$$\mathcal{L}(G_A, G_B, D_A, D_B, S_A, S_B) = \mathcal{L}_{GAN}(G_A, D_A) + \mathcal{L}_{GAN}(G_B, D_B) + \lambda \mathcal{L}_{cyc}(G_A, D_B) + \gamma \mathcal{L}_{shape}(S_A, S_B, G_A, G_B) \quad (5)$$

where parameters λ and γ are weights applied to the cycle-consistency loss and the shape-consistency loss, respectively. In one embodiment, λ is set to 10 and γ is set to 1 during training, however parameters λ and γ can be set to any suitable values to manage or control the relative influence of the cycle-consistency loss and the shape-consistency loss in the overall network performance. To optimize $\mathcal{L}_{GAN}$, $\mathcal{L}_{cyc}$, and $\mathcal{L}_{shape}$, the networks are alternatively updated: $G_{A/B}$ are first optimized with $S_{A/B}$ and $D_{A/B}$ fixed, and then $S_{A/B}$ and $D_{A/B}$ are optimized (they are independent) with $G_{A/B}$ fixed.

Advantageously, generators $G_A$ and $G_B$ are trained with adversarial learning, cycle-consistency loss, and shape-consistency loss and segmentators $S_A$ and $S_B$ are trained using synthesized data from the generators in an online manner. Jointly training generators $G_A$ and $G_B$ and segmentors $S_A$ and $S_B$ is mutually beneficial because, to optimize the composite objective function in Equation (3), the generators have to generate synthesized data with lower shape-consistency loss, which indicates lower segmentation losses over synthesized data, giving rise to better network fitting on a limited amount of real training data.

At step 406 of FIG. 4, the trained generators and segmentors are returned.

Figure 5:
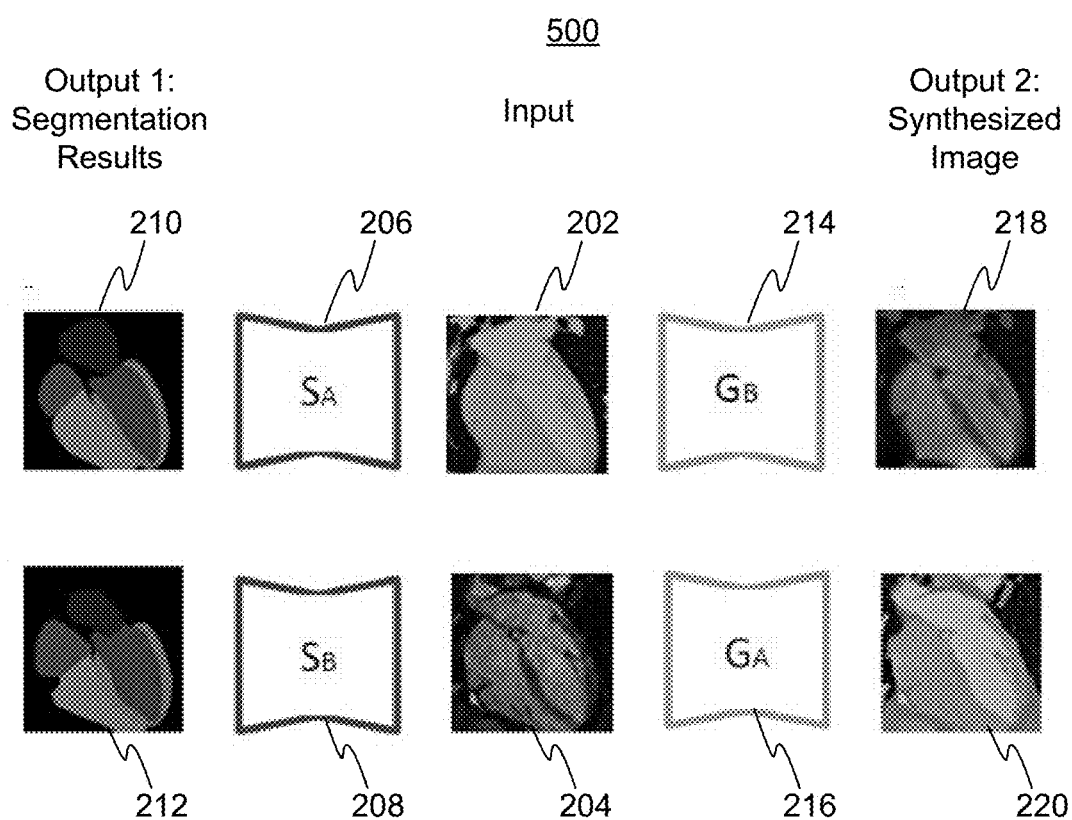
FIG. 5 shows a workflow for applying trained generators and trained segmentors for synthesizing and segmenting input medical images during an online or testing stage, in accordance with one or more embodiments.

FIG. 5 shows a high level workflow 500 for applying trained generators $G_A$ 216 and $G_B$ 214 and trained segmentors $S_A$ 206 and $S_B$ 208 for synthesizing and segmenting input medical images during an online or testing stage, in accordance with one or more embodiments. In one embodiment, trained generators $G_A$ 216 and $G_B$ 214 and trained segmentors $S_A$ 206 and $S_B$ 208 are trained as discussed above with respect to FIGS. 2, 3, and 4. Input medical image 202 is a CT image (denoted as domain A in FIG. 5) and input medical image 204 is an MRI image (denoted as domain B in FIG. 5) of a cardiovascular 2D slice from a 3D volume. Input medical image 202 in domain A is segmented by segmentor $S_A$ 206 to provide segmentation results 210 (e.g., a segmentation mask) of image 202 and translated by generator $G_B$ 214 to generate synthesized image 218 in domain B from image 202. Input medical image 204 in domain B is segmented by segmentor $S_B$ 208 to provide segmentation results 212 of image 204 and translated by generator $G_A$ 216 to generate synthesized image 220 in domain A from image 204.

In one or more embodiments, generators $G_A$ and $G_B$ and segmentors $S_A$ and $S_B$ are trained according network architecture. To train deep networks for training generators $G_A$ and $G_B$ and segmentors $S_A$ and $S_B$, there is a tradeoff between network size (due to memory limitations) and effectiveness. To achieve visually better results, in one embodiment, all networks comprise 3D fully convolutional layers with instance normalization and rectifier linear units (ReLU) for generators $G_A$ and $G_B$ or Leaky ReLU for discriminators $D_A$ and $D_B$. Long-range skip-connection in U-net is used to achieve faster convergence and locally smooth results. 3×3×3 convolution layers with stride 2 and three corresponding upsampling modules are used. There are two convolutions for each resolution. The maximum downsampling rate is 8. Stride 2 nearest upsampling is used followed by a 3×3×3 convolution to realize upsampling and channel changes.

Discriminators $D_A$ and $D_B$ are implemented using patch-GAN to classify whether an overlapping sub-volume is real or fake (i.e., synthetic), rather than classifying the overall volume. Such a strategy avoids the use of unexpected information from arbitrary volume locations to make decisions.

Segmentators $S_A$ and $S_B$ use the U-net like structure but without any normalization layer. 3 times downsampling and upsampling are performed by stride 2 max-poling and nearest upsampling. For each resolution, two sequential 3×3×3 convolutional layers are used.

Generators $G_A$ and $G_B$ and discriminators $D_A$ and $D_B$ may be trained following similar settings in CycleGAN. Segmentators $S_A$ and $S_B$ may be trained using the Adam solver with a learning rate of 2e−4. In one embodiment, generators $G_A$ and $G_B$ and discriminators $D_A$ and $D_B$ may first be pre-trained before jointly training all networks.

In one embodiment, segmentors $S_A$ and $S_B$ may be trained for 100 epochs and generators $G_A$ and $G_B$ for 60 epochs. After jointly training all networks for 50 epochs, the learning rates for both generators $G_A$ and $G_B$ and segmentators $S_A$ and $S_B$ may be decreased for 50 epochs until 0. If the learning rate decreases too much, the synthesized images show more artifacts and segmentators $S_A$ and $S_B$ would tend to overfit. Early stop was applied when segmentation loss no longer decreases for about 5 epochs.

Embodiments of the present invention were experimentally evaluated. 4,354 contrasted cardiac CT scans from patients with various cardiovascular diseases were collected. The resolution inside an axial slice is isotropic and varies from 0.28 mm to 0.74 mm for different volumes. The slice thickness (distance between neighboring slices) is larger than the in-slice resolution and varies from 0.4 mm to 2.0 mm. Residual networks are used with two 2×2 downsampling and upsampling at the head and tail of generators, which are supported by stride-2 convolutions and transpose-convolutions, respectively. In addition, 142 cardiac MRI scans were collected with a new compressed sensing scanning protocol. The MRI volumes have a near isotropic resolution ranging from 0.75 to 2.0 mm. All volumes are resampled to 1.5 mm.

The CT images were denoted as domain A images and the MRI images as domain B images. The data was split in two sets, $S_1$ and $S_2$. For $S_1$, 142 CT images were randomly selected from all CT images to match the number of MRI images. Half of the selected CT images were randomly selected as training data and the remaining half were selected as testing data. For $S_2$, the remaining 4,283 CT images were used as an extra augmentation dataset for generating synthetic MRI images. The testing data in $S_1$ was fixed for all experiments.

Figure 6:
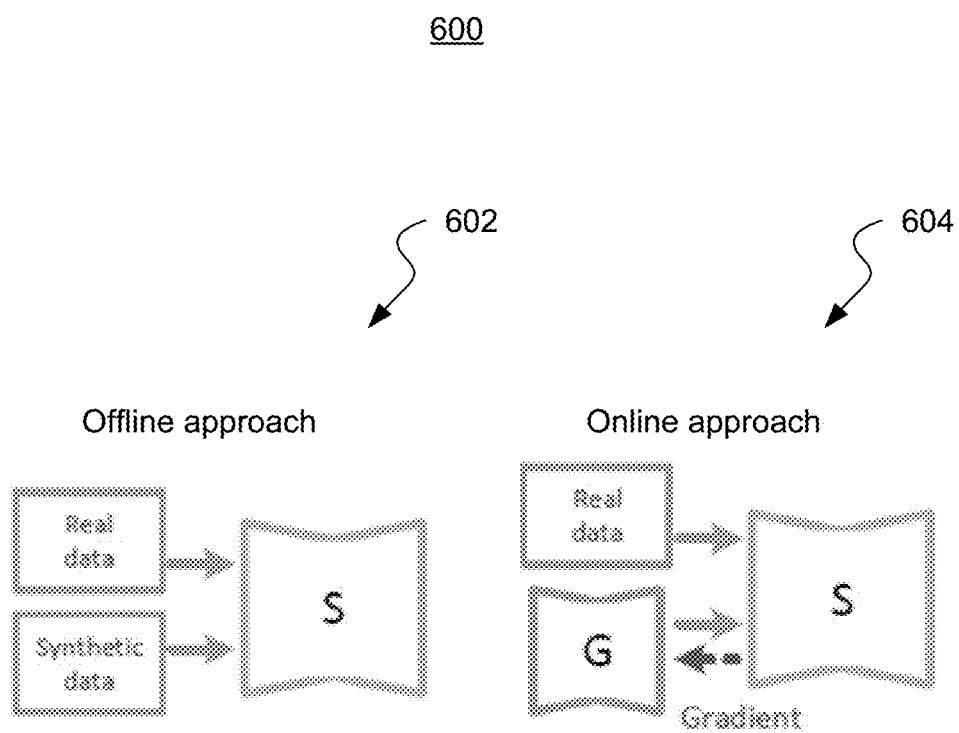
FIG. 6 shows a comparison between a segmentor training workflow using an offline ad-hoc approach (ADA) and a segmentor training workflow using the online approach described in accordance with embodiments of the invention.

FIG. 6 shows an overview 600 of a comparison between a segmentor training workflow using an offline ad-hoc approach (ADA) and a segmentor training workflow using the online approach described in accordance with embodiments of the invention. In the offline approach 602, the segmentor is trained using real data and synthetic data. The synthetic data was generated by generators $\tilde{G}_A$ and $\tilde{G}_B$ (not shown), which were trained with adversarial loss and cycle-consistency loss (without shape-consistency loss). In the online approach 604, segmentors $\tilde{S}_A$ and $\tilde{S}_B$ and generators $\tilde{G}_A$ and $\tilde{G}_B$ were jointly or simultaneously trained (also with the discriminators), and the entire network was fine-tuned in an end-to-end fashion. The training of generators and segmentors in accordance with embodiments of the present invention is referred to as the "online approach". The purpose of the comparison is to evaluate how well the online approach uses synthesized data from the generators to improve segmentation. Two experimental configurations were performed.

The first experiment was conducted on $S_1$ to test how well the online approach improved segmentation with very limited real data. The experiments were performed on both domains A and B. During the training, the amount of training data between the domains A and B can be different due to different experimental configurations.

FIG. 7 shows a table 700 evaluating segmentors trained using a baseline approach, the offline ADA approach, and the online approach. The segmentation results were evaluated based on a dice score reflecting segmentation accuracy. In the baseline approach, the segmentors were trained using only real data, denoted as Baseline(R) in table 702. In the ADA approach, the segmentors were trained using real and synthesized data. In the online approach, the segmentors were trained using real and synthesized data in a joint, end-to-end training with the generators, in accordance with embodiments of the invention. As can be observed, the online approach achieves much better performance on both domains A (CT) and B (MRI). For domain A, the ADA decreases the performance, which may be because the baseline model trained with only 14% real data has not been stabilized. Too much synthesized data distracts optimization when used for ADA.

Figure 8:
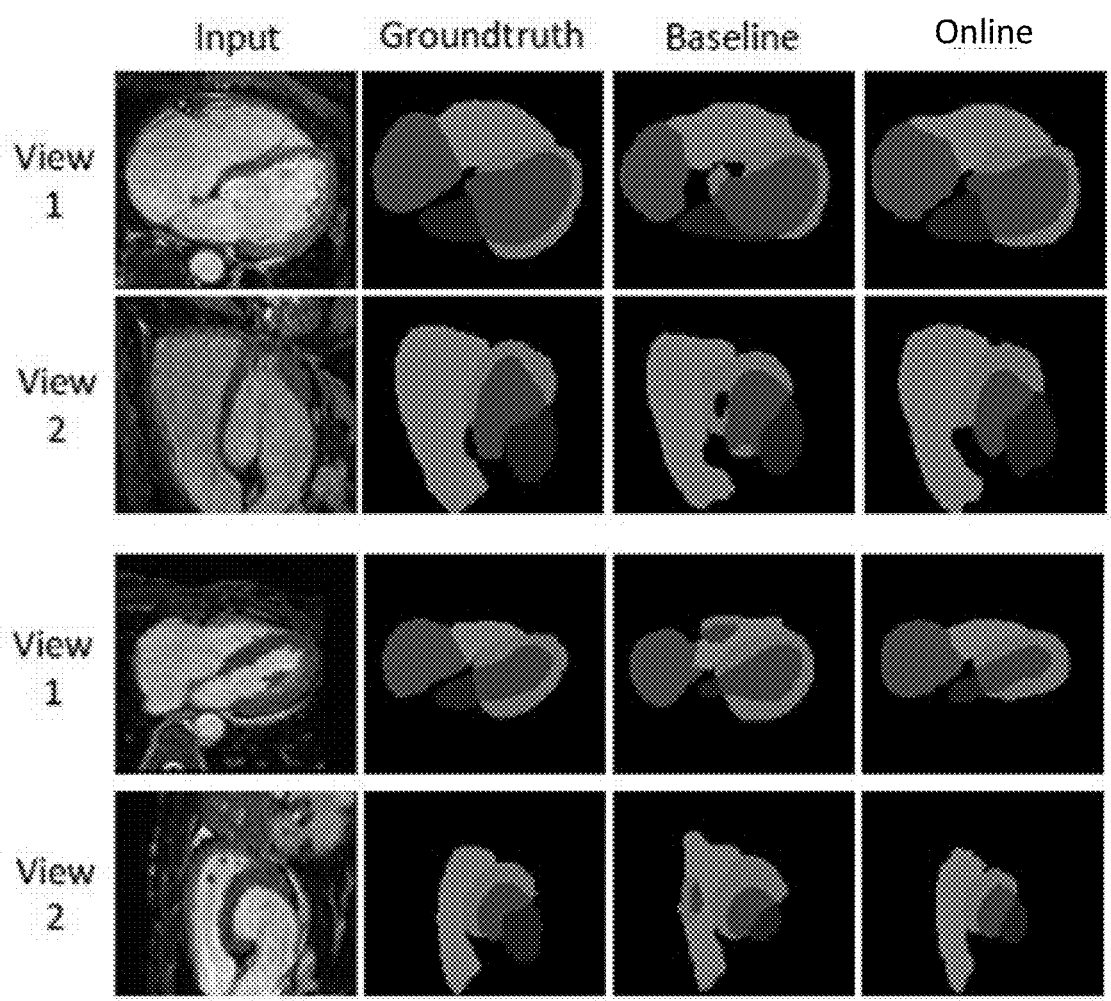
FIG. 8 shows a qualitative evaluation of segmentation results on MRI images.

FIG. 8 shows a qualitative evaluation 800 of segmentation results on domain B (MRI). Evaluation 800 shows a comparison of the initial input medical image, the groundtruth segmentation, segmentation results from a segmentor trained using a baseline model (using real data only), and segmentation results from a segmentor trained using the online approach. View 1 corresponds to the axial view and view 2 corresponds to the sagittal view. As can be seen, the segmentation errors in the baseline have been largely corrected in the online results.

Figure 9:
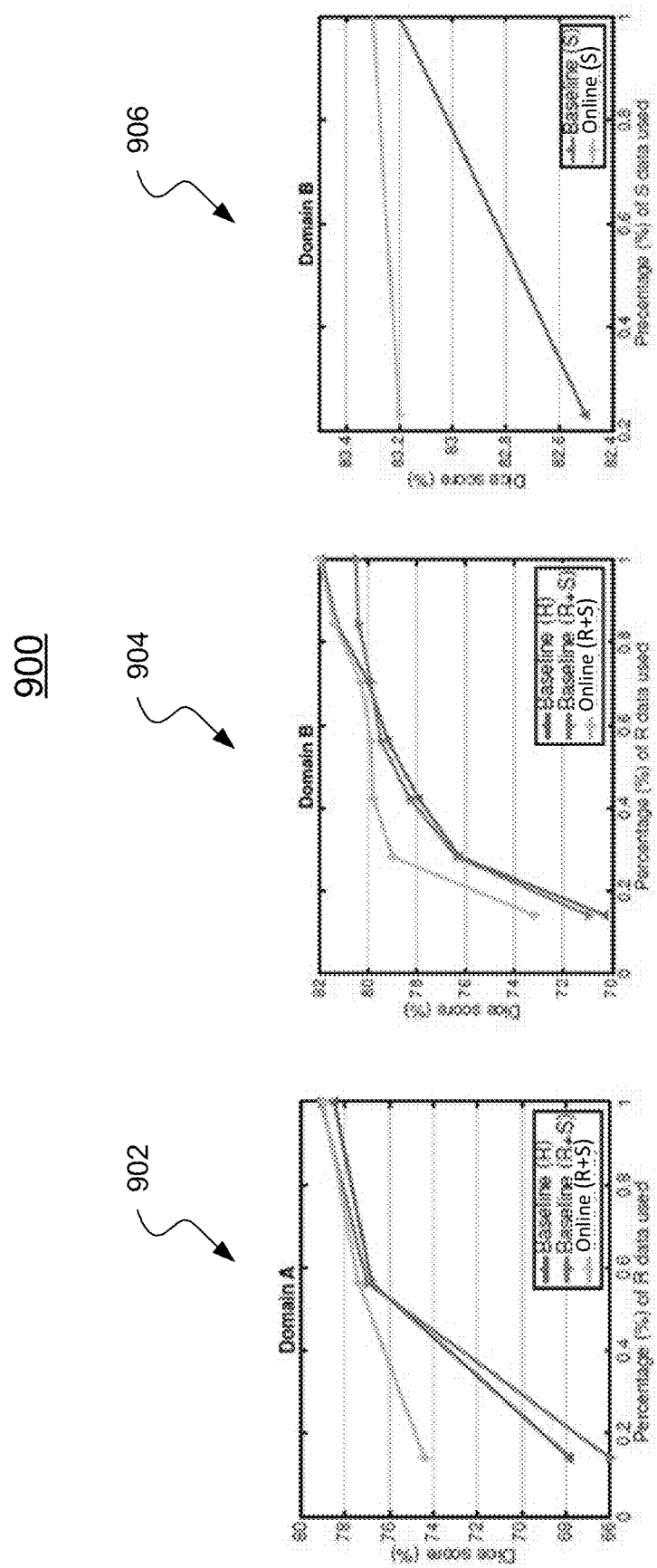
FIG. 9 shows comparisons of segmentation accuracy of the baseline model and the online approach described in accordance with embodiments of the invention.

FIG. 9 shows comparisons 900 of segmentation accuracy of the baseline model and the online approach. With the amount of synthesized data fixed, the amount of real data was varied. Plots 902 and 904 show the results. In plot 902, the segmentation accuracy (Dice score) was compared for a baseline model trained using real data, a baseline model trained using both real and synthesized data, and the online approach trained using both real and synthesized data. The percentage of real data used was varied for training segmentors on domain A using dataset $S_1$, given an equal amount of synthesized data. Plot 904 shows the same experiment as performed for plot 902 but for domain B. Plots 902 and 904 show that the online approach consistently performs the ADA model.

In the second experiment, dataset $S_2$ is applied, which has much more data in domain A. Only synthesized data was used. In plot 906, the segmentation accuracy was compared for a baseline model trained using synthesized data and the online approach trained using synthesized data as the amount of synthesized data was varied. As observed, the online approach performs better than the baseline model. It can also be observed that the online approach uses 23% synthesized data to achieve the performance of ADA using 100% synthesized data.

Figure 10:
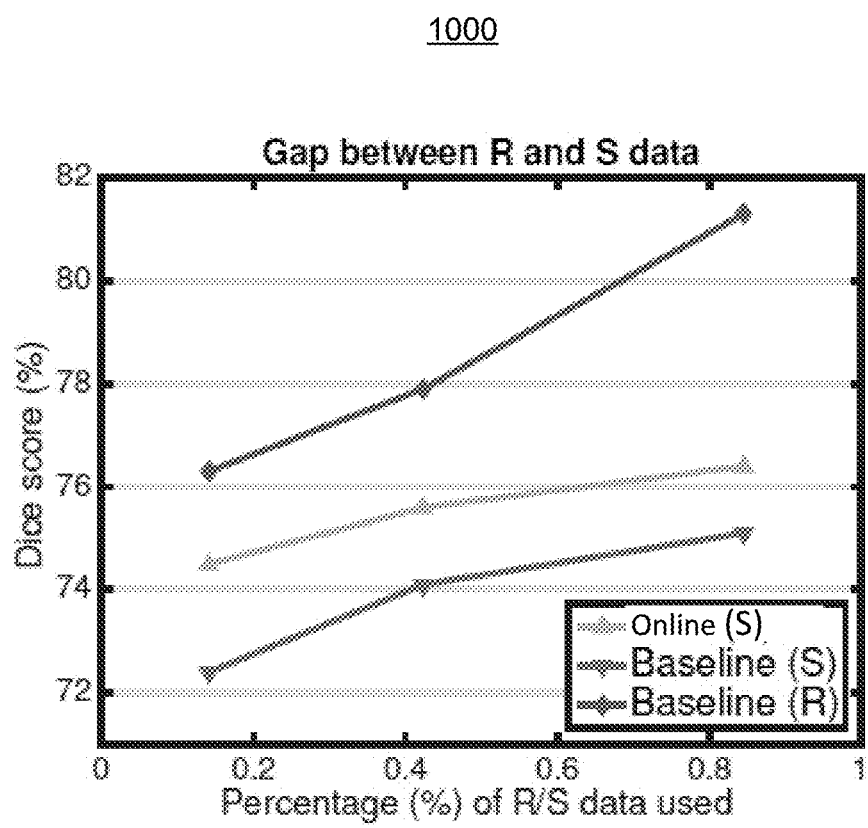
FIG. 10 shows a graph depicting the gap between segmentation performance using real and synthesized data.

FIG. 10 shows a graph 1000 depicting the gap between segmentation performance using real and synthesized data. The gap is defined as the dice score discrepancy between points in an x-axis position. The amount of real or synthesized data used to train the respective segmentation models is varied. On dataset $S_1$, a segmentor is trained using 14% real data from domain B. The accuracy is 70.3%. Then, the segmentation network is trained by using real data for the baseline model, the ADA, and the online approach. As can be seen, the online approach reduces the gap by 61% with 14% real/synthesized data and 20.9% using 85% real/synthesized data.

Figure 11:
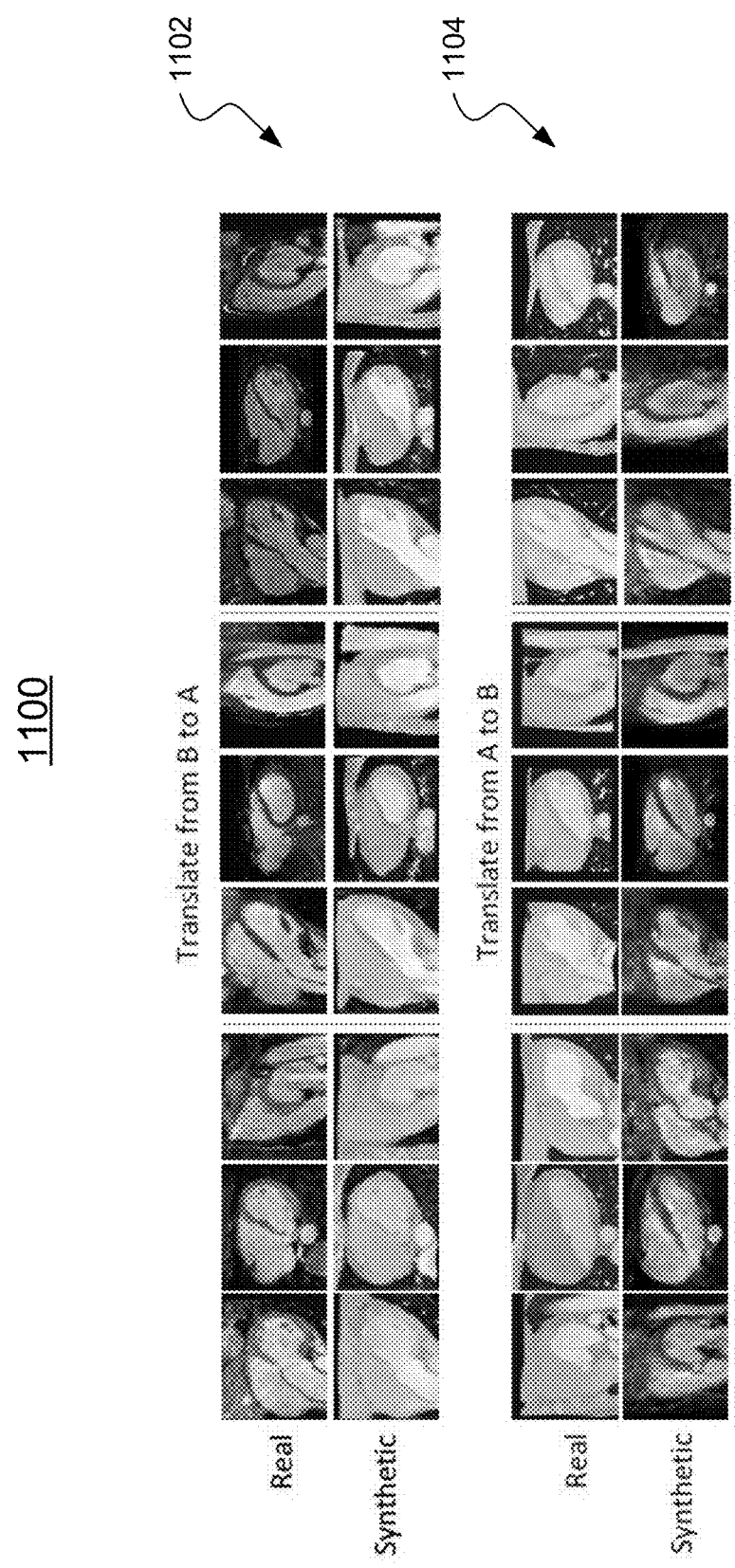
FIG. 11 shows results from a generator trained according to embodiments of the invention.

FIG. 11 shows results 1100 from a generator trained according to embodiments of the invention. Row 1102 shows synthesized images translated from domain A to domain B as compared to real images and row 1104 shows synthesized images translated from domain B to domain A. Visually, the synthetic images are close to real images and no obvious geometric distortion is introduced during image translations.

FIG. 12 shows a table 1200 comparing generators trained without shape consistency (G w/o SC) and generators trained with shape consistence (G w/SC) according to embodiments of the invention. The generators were evaluated based on an S-score (segmentation score). Two segmentation networks were trained on the training data of the respective domains and the multi-class Dice score (used to evaluate the segmentation accuracy) of synthesized 3D volumes was compared. For each synthesized volume, the S-score is computed by comparing to the groundtruth of the corresponding real volume it was translated from. A higher score indicates better matched shape (i.e., pixel-wise label ownership). As can be observed, the generators trained using shape consistent according to embodiments of the invention provided much better shape quality on both domains.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 2-4. Certain steps or functions of the methods and workflows described herein, including one or more of the steps or functions of FIGS. 2-4, may be performed by a server or by another processor in a network-based cloud-computing system. Certain steps or functions of the methods and workflows described herein, including one or more of the steps of FIGS. 2-4, may be performed by a client computer in a network-based cloud computing system. The steps or functions of the methods and workflows described herein, including one or more of the steps of FIGS. 2-4, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 2-4, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 13:
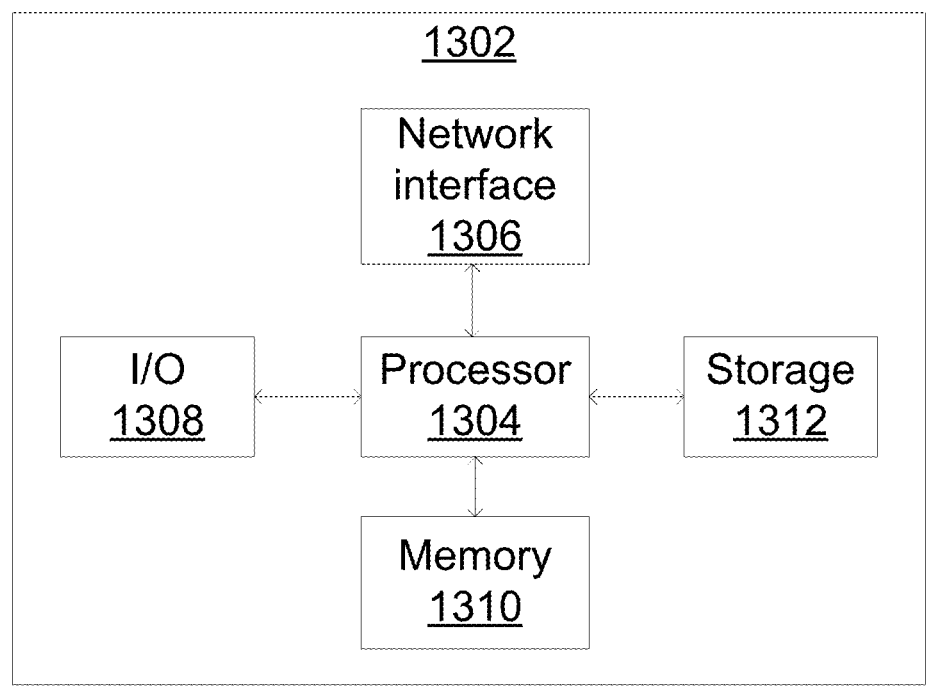
FIG. 13 shows a high-level block diagram of a computer.

A high-level block diagram of an example computer 1302 that may be used to implement systems, apparatus, and methods described herein is depicted in FIG. 13. Computer 1302 includes a processor 1304 operatively coupled to a data storage device 1312 and a memory 1310. Processor 1304 controls the overall operation of computer 1302 by executing computer program instructions that define such operations. The computer program instructions may be stored in data storage device 1312, or other computer readable medium, and loaded into memory 1310 when execution of the computer program instructions is desired. Thus, the method and workflow steps or functions of FIGS. 2-4 can be defined by the computer program instructions stored in memory 1310 and/or data storage device 1312 and controlled by processor 1304 executing the computer program instructions. For example, the computer program instructions can be implemented as computer executable code programmed by one skilled in the art to perform the method and workflow steps or functions of FIGS. 2-4. Accordingly, by executing the computer program instructions, the processor 1304 executes the method and workflow steps or functions of FIGS. 2-4. Computer 1304 may also include one or more network interfaces 1306 for communicating with other devices via a network. Computer 1302 may also include one or more input/output devices 1308 that enable user interaction with computer 1302 (e.g., display, keyboard, mouse, speakers, buttons, etc.).

Processor 1304 may include both general and special purpose microprocessors, and may be the sole processor or one of multiple processors of computer 1302. Processor 1304 may include one or more central processing units (CPUs), for example. Processor 1304, data storage device 1312, and/or memory 1310 may include, be supplemented by, or incorporated in, one or more application-specific integrated circuits (ASICs) and/or one or more field programmable gate arrays (FPGAs).

Data storage device 1312 and memory 1310 each include a tangible non-transitory computer readable storage medium. Data storage device 1312, and memory 1310, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1308 may include peripherals, such as a printer, scanner, display screen, etc. For example, input/output devices 1308 may include a display device such as a cathode ray tube (CRT) or liquid crystal display (LCD) monitor for displaying information to the user, a keyboard, and a pointing device such as a mouse or a trackball by which the user can provide input to computer 1302.

Any or all of the systems and apparatus discussed herein, including elements of workstation 102 of FIG. 1, may be implemented using one or more computers such as computer 1302.

One skilled in the art will recognize that an implementation of an actual computer or computer system may have other structures and may contain other components as well, and that FIG. 13 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method, comprising:
   receiving an input medical image of a patient in a first domain;
   generating a synthesized image in a second domain from the input medical image of the patient in the first domain using a first generator, the first generator trained based on a comparison between segmentation results of a training image in the first domain from a first segmentor and segmentation results of a synthesized training image in the second domain from a second segmentor, the synthesized training image in the second domain generated by the first generator from the training image in the first domain; and
   outputting the synthesized image in the second domain.

2. The method of claim 1, further comprising:
   simultaneously training, in a training stage prior to receiving the input medical image of the patient, the first generator for generating synthesized images in the second domain from images in the first domain, a second generator for generating synthesized images in the first domain from images in the second domain, the first segmentor for segmenting images in the first domain, and the second segmentor for segmenting images in the second domain.

3. The method of claim 2, wherein simultaneously training, in a training stage prior to receiving the input medical image of the patient, the first generator for generating synthesized images in the second domain from images in the first domain, a second generator for generating synthesized images in the first domain from images in the second domain, the first segmentor for segmenting images in the first domain, and the second segmentor for segmenting images in the second domain comprises:
   optimizing a single objective function to train the first generator, the second generator, the first segmentor, and the second segmentor.

4. The method of claim 2, wherein simultaneously training, in a training stage prior to receiving the input medical image of the patient, the first generator for generating synthesized images in the second domain from images in the first domain, a second generator for generating synthesized images in the first domain from images in the second domain, the first segmentor for segmenting images in the first domain, and the second segmentor for segmenting images in the second domain comprises:
   training the first segmentor based on synthesized training images in the first domain generated by the second generator; and
   training the second segmentor based on synthesized training images in the second domain generated by the first generator.

5. The method of claim 1, further comprising:
   segmenting the input medical image of the patient in the first domain using the first segmentor; and
   outputting results of the segmenting the input medical image of the patient in the first domain.

6. The method of claim 1, further comprising:
   receiving a second input medical image in the second domain;
   generating a synthesized image in the first domain from the second input medical image of the patient in the second domain using a second generator, the second generator trained based on a comparison between segmentation results of a second training image in the second domain from the second segmentor and segmentation results of a second synthesized training image in the first domain from the first segmentor, the second synthesized training image in the first domain generated by the second generator from the second training image in the second domain; and
   outputting the second synthesized image in the first domain.

7. The method of claim 6, further comprising:
   segmenting the second input medical image of the patient in the second domain using the second segmentor; and
   outputting results of the segmenting the second input medical image of the patient in the second domain.

8. The method of claim 1, wherein the first generator is trained based on unpaired training images in the first domain and the second domain.

9. The method of claim 1, wherein outputting the synthesized image in the second domain comprises displaying the synthesized image on a display device.

10. An apparatus, comprising:
    means for receiving an input medical image of a patient in a first domain;
    means for generating a synthesized image in a second domain from the input medical image of the patient in the first domain using a first generator, the first generator trained based on a comparison between segmentation results of a training image in the first domain from a first segmentor and segmentation results of a synthesized training image in the second domain from a second segmentor, the synthesized training image in the second domain generated by the first generator from the training image in the first domain; and
    means for outputting the synthesized image in the second domain.

11. The apparatus of claim 10, further comprising:
    means for simultaneously training, in a training stage prior to receiving the input medical image of the patient, the first generator for generating synthesized images in the second domain from images in the first domain, a second generator for generating synthesized images in the first domain from images in the second domain, the first segmentor for segmenting images in the first domain, and the second segmentor for segmenting images in the second domain.

12. The apparatus of claim 11, wherein the means for simultaneously training, in a training stage prior to receiving the input medical image of the patient, the first generator for generating synthesized images in the second domain from images in the first domain, a second generator for generating synthesized images in the first domain from images in the second domain, the first segmentor for segmenting images in the first domain, and the second segmentor for segmenting images in the second domain comprises:

optimizing a single objective function to train the first generator, the second generator, the first segmentor, and the second segmentor.

13. The apparatus of claim 11, wherein the means for simultaneously training, in a training stage prior to receiving the input medical image of the patient, the first generator for generating synthesized images in the second domain from images in the first domain, a second generator for generating synthesized images in the first domain from images in the second domain, the first segmentor for segmenting images in the first domain, and the second segmentor for segmenting images in the second domain comprises:

means for training the first segmentor based on synthesized training images in the first domain generated by the second generator; and means for training the second segmentor based on synthesized training images in the second domain generated by the first generator.

14. The apparatus of claim 10, further comprising:

means for segmenting the input medical image of the patient in the first domain using the first segmentor; and means for outputting results of the segmenting the input medical image of the patient in the first domain.

15. A non-transitory computer readable medium storing computer program instructions, the computer program instructions when executed by a processor cause the processor to perform operations comprising:

receiving an input medical image of a patient in a first domain;

generating a synthesized image in a second domain from the input medical image of the patient in the first domain using a first generator, the first generator trained based on a comparison between segmentation results of a training image in the first domain from a first segmentor and segmentation results of a synthesized training image in the second domain from a second segmentor, the synthesized training image in the second domain generated by the first generator from the training image in the first domain; and outputting the synthesized image in the second domain.

16. The non-transitory computer readable medium of claim 15, the operations further comprising:

simultaneously training, in a training stage prior to receiving the input medical image of the patient, the first generator for generating synthesized images in the second domain from images in the first domain, a second generator for generating synthesized images in the first domain from images in the second domain, the first segmentor for segmenting images in the first domain, and the second segmentor for segmenting images in the second domain.

17. The non-transitory computer readable medium of claim 16, wherein simultaneously training, in a training stage prior to receiving the input medical image of the patient, the first generator for generating synthesized images in the second domain from images in the first domain, a second generator for generating synthesized images in the first domain from images in the second domain, the first segmentor for segmenting images in the first domain, and the second segmentor for segmenting images in the second domain comprises:

optimizing a single objective function to train the first generator, the second generator, the first segmentor, and the second segmentor.

18. The non-transitory computer readable medium of claim 15, the operations further comprising:

receiving a second input medical image in the second domain;

generating a synthesized image in the first domain from the second input medical image of the patient in the second domain using a second generator, the second generator trained based on a comparison between segmentation results of a second training image in the second domain from the second segmentor and segmentation results of a second synthesized training image in the first domain from the first segmentor, the second synthesized training image in the first domain generated by the second generator from the second training image in the second domain; and outputting the second synthesized image in the first domain.

19. The non-transitory computer readable medium of claim 18, the operations further comprising:

segmenting the second input medical image of the patient in the second domain using the second segmentor; and outputting results of the segmenting the second input medical image of the patient in the second domain.

20. The non-transitory computer readable medium of claim 15, wherein the first generator is trained based on unpaired training images in the first domain and the second domain.

* * * * *